US011359733B2

(12) United States Patent
Oddo et al.

(10) Patent No.: US 11,359,733 B2
(45) Date of Patent: Jun. 14, 2022

(54) CHECK VALVE

(71) Applicant: Aires Medical LLC, Ann Arbor, MI (US)

(72) Inventors: Nicholas Leonard Oddo, Hilton Head Island, SC (US); Shane Woody, Mooresville, NC (US); Chad Josey, Mooresville, NC (US); Dylan Moore, Mooresville, NC (US)

(73) Assignee: BEECH HEALTH, INC., Ann Arbor, MI (US)

( * ) Notice: Subject to any disclaimer, the term of this patent is extended or adjusted under 35 U.S.C. 154(b) by 0 days.

(21) Appl. No.: 16/996,070

(22) Filed: Aug. 18, 2020

(65) Prior Publication Data

US 2020/0386333 A1 Dec. 10, 2020

Related U.S. Application Data

(63) Continuation-in-part of application No. 16/704,413, filed on Dec. 5, 2019.
(Continued)

(51) Int. Cl.
*A61M 16/20* (2006.01)
*F16K 15/03* (2006.01)
(Continued)

(52) U.S. Cl.
CPC ....... *F16K 15/036* (2013.01); *A61M 16/0875* (2013.01); *A61M 16/208* (2013.01);
(Continued)

(58) Field of Classification Search
CPC .... A61M 1/101; A61M 1/1032; A61M 1/106; A61M 1/1062; A61M 1/1065;
(Continued)

(56) References Cited

U.S. PATENT DOCUMENTS 2,692,609 A * 10/1954 Carter ..................... F16K 31/34
141/219
2,972,345 A * 2/1961 Spigel ............... A61M 16/0009
128/204.23
(Continued)

OTHER PUBLICATIONS

Matthew M. Gangidine et al., "System Design Verification for Closed Loop Control of Oxygenation With Concentrator Integration", Military Medicine, vol. 181, p. 177-183, May 2016.

*Primary Examiner* — Annette Dixon
(74) *Attorney, Agent, or Firm* — Caldwell Intellectual Property Law; Katherine Rubino

(57) ABSTRACT

A check valve can include a pressure actuator or an electromagnetic actuator. The check valve includes a valve inlet, a valve outlet, and flap disposed between the valve inlet and the valve outlet. The pressure actuator in fluid communication with the valve inlet. The check valve has an open state and a closed state. The check valve is configured to allow an input gas to flow from the valve inlet to the valve outlet when the check valve is in the open state. The check valve is configured to preclude the input gas from flowing from the valve inlet to the valve outlet when the check valve is in the closed state. Upon actuation of the pressure actuator or the electromagnetic actuator, the flap moves away from the valve inlet to allow the inlet gas to move from the valve inlet to the valve outlet.

8 Claims, 4 Drawing Sheets

Related U.S. Application Data

(60) Provisional application No. 63/047,742, filed on Jul. 2, 2020, provisional application No. 62/775,733, filed on Dec. 5, 2018.

(51) Int. Cl.
*A61M 16/08* (2006.01)
*F16K 15/18* (2006.01)
*A61M 16/00* (2006.01)

(52) U.S. Cl.
CPC . *F16K 15/1821* (2021.08); *A61M 2016/0027* (2013.01); *A61M 2230/40* (2013.01)

(58) Field of Classification Search
CPC ........ A61M 1/12; A61M 1/125; A61M 16/00; A61M 16/0009; A61M 16/0051; A61M 16/0069; A61M 16/021; A61M 16/024; A61M 16/10; A61M 16/107; A61M 16/12; A61M 16/20; A61M 16/202; A61M 16/204; A61M 16/206; A61M 2016/0021; A61M 2016/0039; A61M 2016/1025; A61M 2205/3365; A61M 2205/70; B64B 1/62; B64B 1/64; F16K 15/147; F16K 15/185; F16K 31/0672; F16K 31/0675; F16K 31/34; F16K 7/045; Y10T 137/7297

See application file for complete search history.

(56) References Cited

U.S. PATENT DOCUMENTS

| | | | | |
|---|---|---|---|---|
| 4,957,107 | A | * | 9/1990 | Sipin ................. A61M 16/0051 128/204.21 |
| 5,664,562 | A | * | 9/1997 | Bourdon ........... A61M 16/0069 128/204.18 |
| 6,484,721 | B1 | | 11/2002 | Bliss |
| 9,097,361 | B1 | * | 8/2015 | Ratner ................ F16K 31/0672 |
| 9,724,017 | B2 | | 8/2017 | Baloa Welzien et al. |
| 10,046,134 | B2 | | 8/2018 | DeVries et al. |
| 10,245,406 | B2 | | 4/2019 | DeVries et al. |
| 10,265,486 | B2 | | 4/2019 | Allum et al. |
| 10,315,002 | B2 | | 6/2019 | DeVries et al. |
| 2003/0180164 | A1 | * | 9/2003 | Bunner ................. F04B 43/025 417/413.1 |
| 2021/0001075 | A1 | * | 1/2021 | Oddo ................. A61M 16/026 |
| 2021/0038856 | A1 | * | 2/2021 | Oddo ................. A61M 16/201 |

* cited by examiner

CHECK VALVE

CROSS-REFERENCE TO RELATED APPLICATIONS

This application claims priority, and the benefit of, U.S. Provisional Patent Clean Specification Application No. 63/047,742, filed Jul. 2, 2020, U.S. patent application Ser. No. 16/704,413, filed on Dec. 5, 2019, which in turn claims priority, and the benefit of, U.S. Provisional Patent Application 62/775,733, filed on Dec. 5, 2018, each of which is hereby incorporated by reference in its entirety.

TECHNICAL FIELD

The present disclosure generally relates to a medical device, and more particularly, to a mechanical ventilator with a check valve.

BACKGROUND

Check valve can include a passage with an inlet opening and an outlet opening. A check valve is arranged in the passage and is configured to allow fluid flow in one direction and preclude fluid flow in an opposite direction.

SUMMARY

The present disclosure describes a check valve. The check valve includes a valve inlet, a valve outlet, and a pressure actuator in fluid communication with the valve inlet. The check valve further includes a flap disposed between the valve inlet and the valve outlet. The flap includes a first flap portion and a second flap portion. The check valve has an open state and a closed state. The check valve is configured to allow an input gas to flow from the valve inlet to the valve outlet when the check valve is in the open state. The check valve is configured to preclude the input gas from flowing from the valve inlet to the valve outlet when the check valve is in the closed state. Upon actuation of the pressure actuator, the first flap portion and the second flap portion separate from each other to allow the input gas to flow from the valve inlet to the valve outlet of the check valve.

In another aspect of the present disclosure, the check valve includes a valve inlet, a valve outlet, a flap disposed between the valve inlet and the valve outlet, and an electromagnetic actuator coupled to the flap. The check valve has an open state and a closed state. The check valve is configured to allow an input gas to flow from the valve inlet to the valve outlet when the check valve is in the open state. The check valve is configured to preclude the input gas from flowing from the valve inlet to the valve outlet when the check valve is in the closed state. Upon actuation of the electromagnetic actuator, the flap moves away from the valve inlet to allow the input gas to flow from the valve inlet to the valve outlet of the check valve. The check valves described above can be part of a ventilator.

The above features and advantages and other features and advantages of the present teachings are readily apparent from the following detailed description of the modes for carrying out the present teachings when taken in connection with the accompanying drawings.

BRIEF DESCRIPTION OF THE DRAWINGS

The accompanying drawings, which are incorporated into and constitute a part of this specification, illustrate implementations of the disclosure and together with the description, serve to explain the principles of the disclosure.

DETAILED DESCRIPTION

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property can include additional elements not having that property.

Figure 1A:
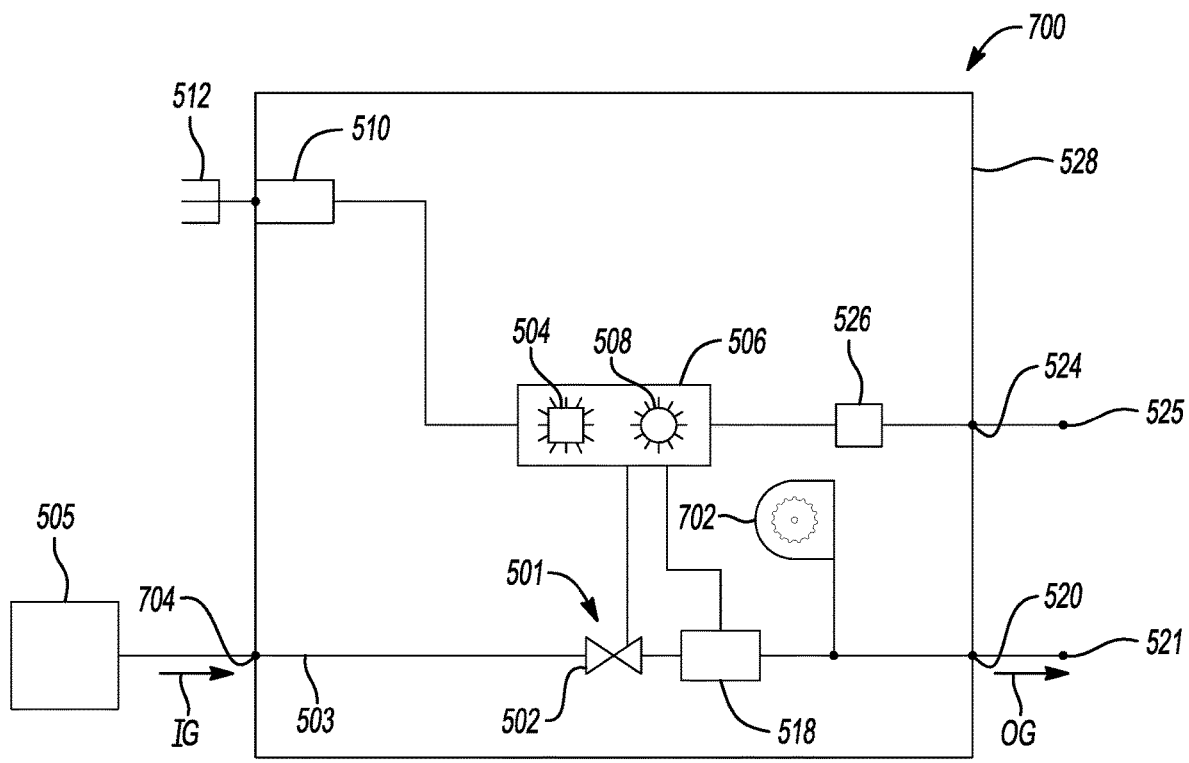
FIG. 1A is a schematic illustration of a ventilator that uses an ultra-low pressure gas source, and a turbine blower configured to add energy to increase the pressure of the gas.

With reference to FIG. 1A, a ventilator 700 includes a valve 502, such as an electronically controlled solenoid valve or an on-off valve, configured to modulate compressed oxygen or air sources. Accordingly, the valve 502 has at least an open state and a closed state. The valve 502 can be part of a valve arrangement 501. The valve arrangement 501 can therefore include one or more of valve 502. It is also contemplated that the valve arrangement 501 can include other types of valves. Hence, the ventilator 700 can include a single valve 502 to minimize cost and weight. The ventilator 700 functions by receiving input gas IG from an input gas source 505 through a tubing 503. As non-limiting examples, the input gas source 505 can be an air compressor, air blower, stationary oxygen concentrator, portable oxygen concentrator, air tank, and/or oxygen tank. A continuous flow of input gas IG enters the ventilator 700 through an inlet 704 of the tubing 503, and when the valve 502 opens, the flow rate of input gas IG and output gas OG is the same or at least substantially the same.

The ON-OFF cycles of the valve 502 are controlled using a controller 504, such as a microprocessor or microcontroller unit. The controller 504 can be part of an electronic board 506, which can contain additional electronic components including but not limited to: power electronics, resistors, capacitors, alarms, and copper traces. The electronic board 506 can include one or more alarm 508. Alarm 508 can, for example, be used to warn the user of one or more of the following conditions: tubing disconnections, electrical or air supply failure, high peak airway pressure, auto-positive end-expiratory pressure (auto-PEEP), high gas supply pressures, and/or no spontaneous breathing. Further, this electronic board 506 can be utilized as a battery management system for a portable ventilator device that is battery powered.

The ventilator 700 can include electrical power source 510, such as a portable rechargeable Li-Ion battery pack or another suitable portable battery assembly. The electrical power source 510 (e.g., battery pack) can include a recharging interface 512, such as a port or cable, thereby allowing the electrical power source 510 to be recharged. As non-limiting examples, the recharging interface 512 can be a Universal Serial Bus-C (USB-C), a USB, a micro-USB, or other charging interfaces. The electrical power source 510 can be electrically connected to the electronic board 506 to supply electricity to the controller 504 and the alarm 508.

This controller 504 can be in the form of an FPGA, MCU, single board computer, ASIC, PLC on a chip, and/or other processing or computer hardware that can control the ON/OFF or OPEN/CLOSE cycles of the valve 502 (e.g., solenoid valve). The valve 502 can be controlled using fluidic chips or other non-conventional or pneumatic methods of valve control, such as air cylinder actuations.

The flow rate of this continuous gas output to the patient (i.e., the output gas OG) is measured using a flow sensor 518. This flow sensor 518 can be in electric communication with the controller 504 and can comprise a plurality of sensor methodologies. For example, the flow sensor 518 can utilize the thermo-transfer principle, also known as the calorimetric principle, to measure large ranges of gas flow rates when the gain factor of the flow sensor 518 is specifically calibrated and tested, such that the sensor output is amplified and two point trimmed at zero flow as well as a secondary flow rate point to optimize linearity within a certain flow rate range, such as 0-40 standard liter per minute (SLPM) gas flow. Under this thermo-transfer principle, inside the flow sensor 518, a temperature sensor (not shown) is heated periodically by a heater element (not shown). The flowing gas absorbs heat energy and conducts it away. The resulting temperature change is an indication of flow, which translates to an analog voltage value that is then correlated to a flow output curve based on experimental data from the original equipment manufacturer (OEM) or sensor manufacturer during calibration and/or testing. Generally, this flow sensor 518 is a flow-through type sensor, wherein the flow sensor 518 includes a barb fitting inlet that connects to the oxygen or tubing 503, as well as a barb outlet to the flow outlet airline 520 with minimal resistance of fluidic loss. This flow outlet airline 520 can connect to a 22 mm breathing tube, hose barb, adapter, or other tubing connection thereafter. The flow sensor 518 can alternatively be other types of sensors, such as: turbine-type flow meters, rotometers, and membrane based differential pressure and temperature sensors that can be used to calculate flow rates, which can work especially well for laminar type or large volume/low pressure flows. the flow outlet airline 520 includes an airline outlet 521.

During operation, user spontaneous breathing is detected using a separated breath detection airline 524 and a pressure sensor 526 for measuring breathing pressures (e.g., nasopharynx pressure). The breath detection airline 524 includes an airline inlet 525. The airline inlet 525 is separated from the airline outlet 521 of the flow outlet airline 520 to minimize interference and therefore increase the accuracy of the pressure sensor 526. The pressure sensor 526 is in fluid communication with the breath detection airline 524. This breath detection airline 524 is configured to be connected to a 22 mm breathing tube, hose barb, adapter, or other tubing connection. The breath detection airline 524 is not in direct fluid communication with the flow outlet airline 520. By fluidly separating the breath detection airline 524 from the flow outlet airline 520, the breathing pressures (e.g., nasopharynx pressures) can be measured without signal interference from the pressure/flow output from the ventilator 700, which would otherwise saturate the pressure sensor 526 required to measure the breathing pressures (e.g., nasopharynx pressures). In other ventilators and oxygen concentrators, a single airline is generally utilized in which a flow or pressure trigger threshold, ex. $-0.13$ cm $H_2O$ pressure, is used to determine the start of inhalation. This generally creates substantial lag in the ventilator gas output or false breathing triggers. Further, this necessitates the use of far less sensitive pressure sensors to prevent the pressure sensor from getting saturated from the output flow gas from the ventilator. Also, if flow is triggered based on a flow ramp, there can still exist substantial signal interference using a single airline.

In the presently disclosed ventilator 700, a breath detection software is used to predict transitions in breathing states and breathing time states, for example: transition from inhale to exhale, 70% inhalation time, transition from exhale to inhale, predicted PEEP based on % of exhalation. This breath detection software functions by measuring breathing pressures (e.g., nasopharynx pressures) using a separated breath detection airline 524, then storing the voltage values from the pressure sensor 526 in the controller 504 (e.g., microcontroller) RAM or EEPROM. For this reason, the controller 504 is in electronic communication with the pressure sensor 526. Breath transition states and timing predictions are detected through one or more mathematical calculations involving the pressure sensor voltage data including but not limited to: data filtering, differentiation, integration, linear regression analysis and linearizations, moving average calculations, Taylor series approximations, steady state error compensation, model predictive control, proportional control, fuzzy control theory, ODEs, radial basis functions, quadratic-program approximation, feedforward control, adaptive control, PI and/or PID control, SISO control schema, Laplace transformations. A moving average calculation can be used such that, if the filtered pressure sensor data falls below the moving average, a transition from an inhale to an exhale is predicted.

Other sensors can also be used independently, in combination with, or to replace the pressure sensor 526 described herein to measure data trends in breathing, implement predictive breath detection software algorithms, and/or actuate at certain threshold values and/or ramps including but not limited to: flow sensors, CO2 gas concentration sensors, O2 gas concentration sensors, temperature sensors, humidity sensors, volume sensors, and/or acoustic sensors. This breath detection is used to determine when to output ventilator gas, which can include compressed air, oxygen, or a mixture thereof, to the patient at the correct time in order to provide pressure/ventilatory support, as well as facilitate effective lung gas exchange, ventilation, and manage arterial blood gases (ABGs) such as $PaCO_2$ and $PaO_2$. Accordingly, the pressure sensor 526 is configured to generate sensor data indicative of breathing by the user, and the controller 504 is programmed to detect the breathing of the user based on the sensor data received from the pressure sensor 526.

The components and electromechanical subassemblies of the ventilator 700 are contained within an enclosure 528, which can be manufactured using a plurality of manufacturing methods including but not limited to: injection molding, 3D printing, CNC machining, sheet metal fabrication, PCBA, wire harnessing, and other manual or automated manufacturing techniques not described herein.

The ventilator 700 uses one or more input gas sources 505 where the one or more input gas sources may include ultra low pressure gas sources. The ventilator 700 includes a turbine 702 in fluid communication with the tubing 503. The turbine 702 adds energy to increase pressure of the output gas OG, thereby allowing the flow restrictions to be minimized. Accordingly, the ventilator 700 can use smaller tubing patient interfaces (e.g., flow outlet airline 520 and breath detection airline 524). In other CPAP devices and ventilators, a large bore breathing tubing (e.g., 22 mm diameter tubing) is used due to the low pressure gas output, which generally ranges from 4-20 cm $H_2O$ pressure. In some cases, this air entrainment ratio can exceed 25 times the amount of volume/flow rate of the input gas flow. Oxygen concentrators or generation devices can be used to generate ultra-low oxygen output pressures in order to minimize the energy consumption of the gas separation process. Assuming 2 LPM oxygen gas is produced at 0.6 PSIG output pressure and 49 LPM of air entrainment, this would result in a total pressure for the air-$O_2$ mixture of 0.024 PSIG. Based on flow coefficient calculations, this would mean only 32.35 LPM of gas with a 0.024 PSI pressure differential can flow through a 10 mm circular patient interface orifice. Hence, if a discreet and small bore tubing were to be used as the patient interface, for example with a dual lumen nasal cannula or oxygen eyeglass frames with nasal pillows, either lower amounts of air entrainment or higher pressure oxygen gas would be required for the patient interface to be feasible. Hence, in the ventilator 700, the turbine 702 is used to increase the pressure of the input gas IG in the oxygen from an oxygen concentrator (not shown) or gas source from an inlet 704 that is in fluid communication with the tubing 503. The valve 502 is in fluid communication with the tubing 503. The input gas flowing from inlet 704 flows through a valve 502 (e.g., a solenoid valve or check valve) and is measured by the flow sensor 518. The input gas IG from the inlet 704 flows through the valve 502, and then flows to the turbine 702. Hence, the pressure of the air-$O_2$ mixture is increased by adding energy into the ventilator 700. For example, if the pressure of the air-$O_2$ gas mixture increases from 0.024 PSIG to 0.146 PSIG, then 19.7 LPM of gas can flow through ventilator tubing 503 with a 2.4 $mm^2$ orifice cross sectional area. This would make, for example, a pair of discreet oxygen eyeglasses that utilizes two separate 1.2 mm diameter by 2 mm oval air channels feasible with 40 LPM of flow through the patient circuit.

Alarm 508 may be an audible safety alarm in the ventilator 700 designed for medical applications for use in ventilation equipment, and preferably certified such that this audible safety alarm is recognized under the IEC 60601-1-8 standard. This alarm 508 is a component of the electronic board 506 that can include a specially designed speaker-housing assembly with no circuitry. Other alarm types can also be utilized including but not limited to: piezoelectric type speakers, audio amplifiers, and/or electromagnetic speakers. With this alarm 508, the OEM only needs to input a simple square wave signal with one frequency component, and the other needed harmonic sound frequencies are generated acoustically. This greatly simplifies implementation of an audible alarm sound in an IEC 60601-1-8. This alarm relies on the 2nd option for compliance, a melody table listed in Annex F of the IEC 60601-1-8 standard where specific medical conditions/applications are assigned individual melodies. These melodies are essentially little tunes that change in pitch per the tables in Annex F. The objective is that the medical personnel using medical equipment with alarms that use these melodies will become familiar with them which can help the medical personnel respond more quickly and more appropriately when a specific melody alarm is sounded. This ventilator 700 utilizes the alarm 508 to generate high, medium, or low priority warning sound depending on the condition of the patient or malfunctions with ventilator equipment such as tubing disconnects. The audible sound has fundamental frequency <1000 Hz, with at least 4 harmonic frequencies within ±15 dB of the fundamental frequency. This alarm 508 has a specific waveform and timing requirements for the three priority sounds, which includes a sound rise time specified by the alarm manufacturer. Alarm settings can include, but are not limited to, the following: if $O_2$ input from inlet 704 flows, but no breathing/exhalation is detected within 6 seconds, if the electrical power source 510 is being used, or if $O_2$ connected in wrong conduit (e.g., breath detection airline 524 or flow outlet airline 520).

Figure 1B:
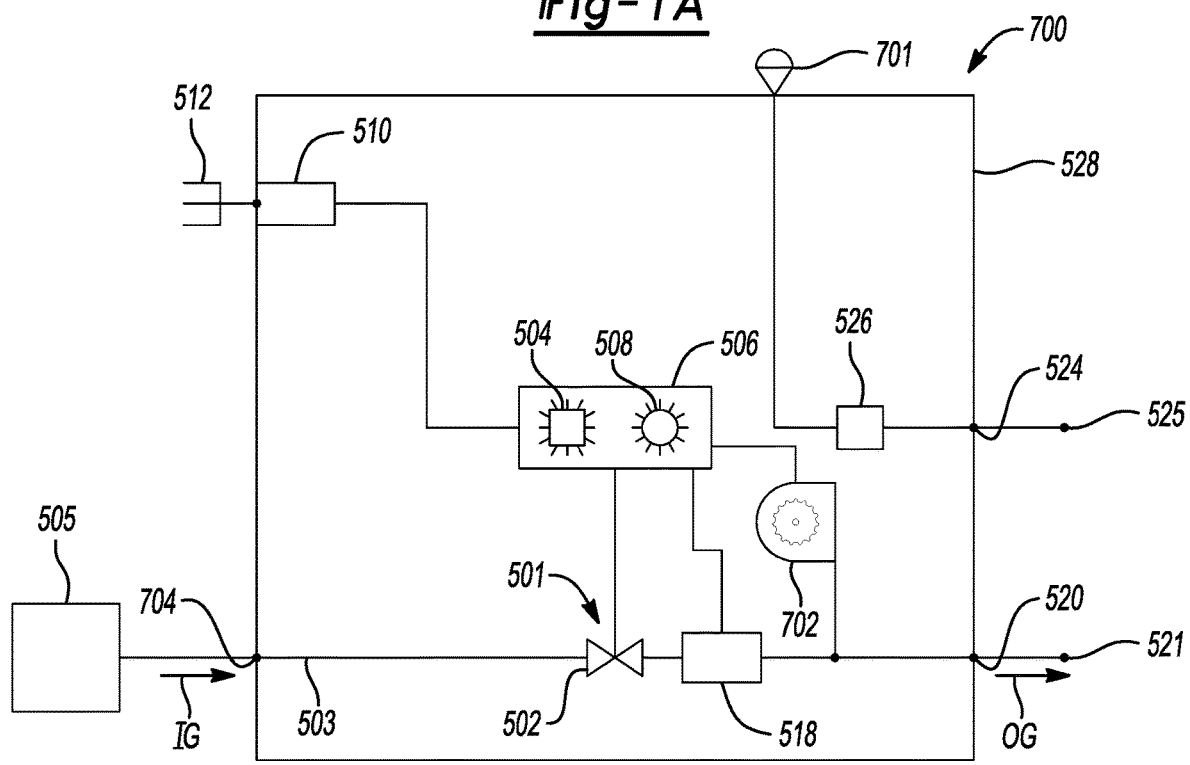
FIG. 1B is a schematic illustration of a ventilator that uses a PEEP valve.

In some embodiments as shown in FIG. 1B, the ventilator 700 can include a positive end-expiratory pressure (PEEP) valve 701. PEEP valve 701 may include a mechanical or pneumatic valve. The PEEP valve 701 is in fluid communication with the breath detection airline 524. In the present disclosure, term "PEEP valve" means a spring loaded valve that receives the pressure of the patient's exhalation to open and close. In other words, the pressure of the patient's exhalations acts on the PEEP valve 701, causing the PEEP valve 701 to open or close. Specifically, the PEEP valve 701 is configured to close when the pressure of the patient's exhalation is equal to or less than a predetermined pressure threshold to retain exhalation volume in the lungs. In doing so, the PEEP valve 701 increases the volume of gas remaining in the lungs at the end of expiration of the user of the ventilator 700 in order to decrease the shunting of blood through the lungs and improve gas exchange. When the pressure of the patient's exhalation is greater than the predetermined pressure threshold, the PEEP valve 701 opens. In order for the PEEP valve 701 to open and close at appropriate pressure as discussed above, the PEEP valve 701 can be in direct fluid communication with the breath detection airline 524. The PEEP valve 701 can be disposed outside the enclosure 528 to facilitate expunging exhalation gases from the user of the ventilator 700.

Figure 1C:
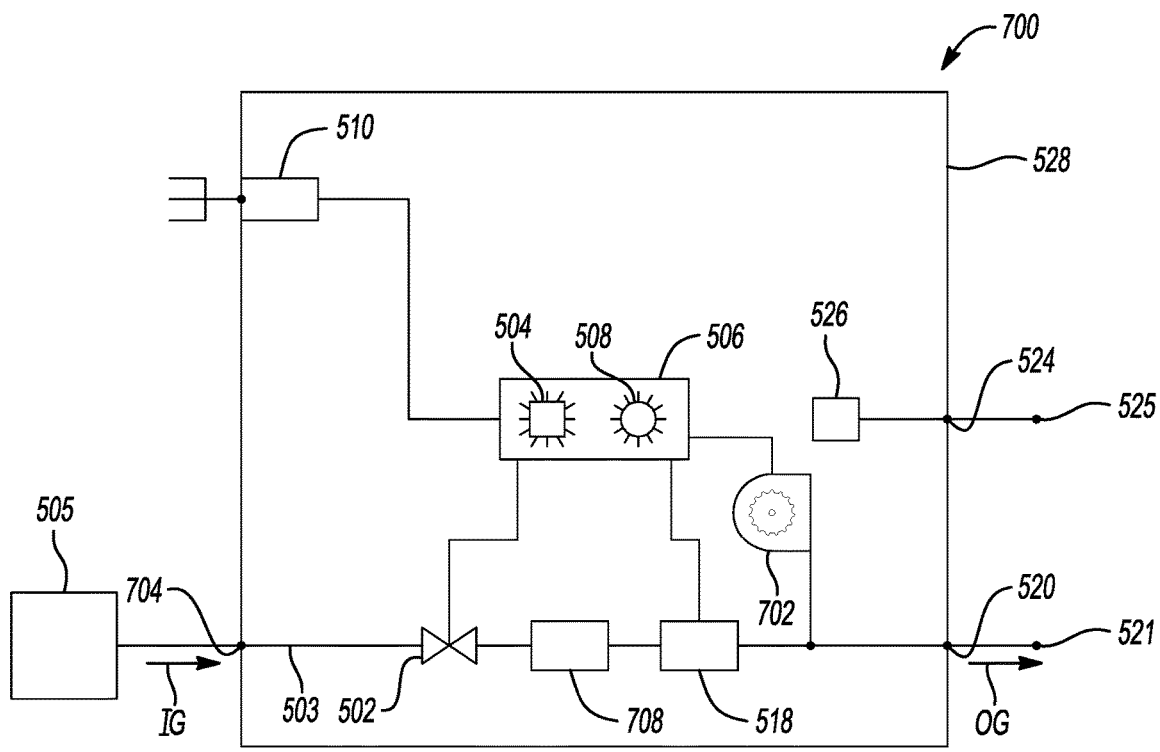
FIG. 1C is a schematic illustration of a ventilator that uses an oxygen concentrator.

In some embodiments as shown in FIG. 1C, the ventilator 700 can include an internal oxygen concentrator 708, which can be fluidly connected to allow external gas sources. This internal oxygen concentrator 708 can be of several types, such as, but is not limited to: pressure swing adsorption, vacuum pressure swing adsorption, ultra-rapid pressure swing adsorption, oscillator pressure swing adsorption, "molecular gate" pressure swing adsorption, thermally cycled pressure swing adsorption, thermal swing adsorption, Joule-Thomson liquefaction units for the production of liquid oxygen from atmospheric air, gaseous oxygen tanks, liquid oxygen tanks, membrane based gas separation units, and combinations thereof.

Figures 2A, 2B:
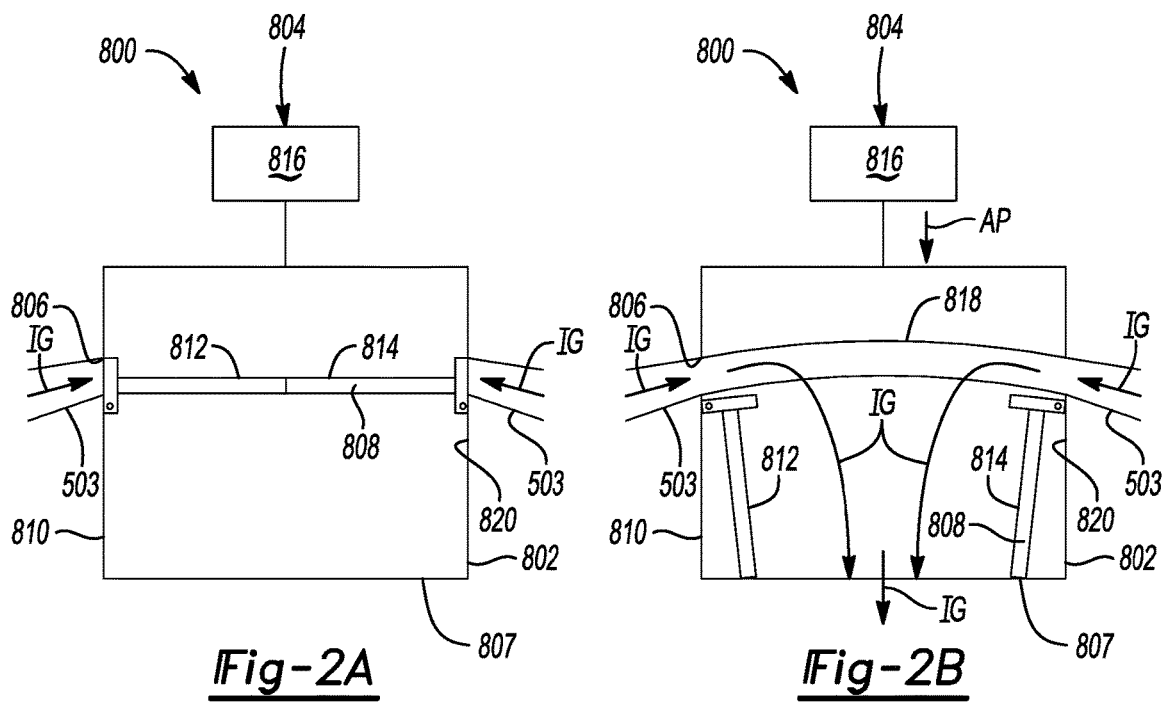
FIG. 2A is a schematic cross-sectional view of an electronically controlled check valve using pressure actuators, wherein the electronically controlled check valve is shown in an OFF state.
FIG. 2B is a schematic cross-sectional view of the electronically controlled check valve of FIG. 2A shown in an ON state.
Figure 3A:
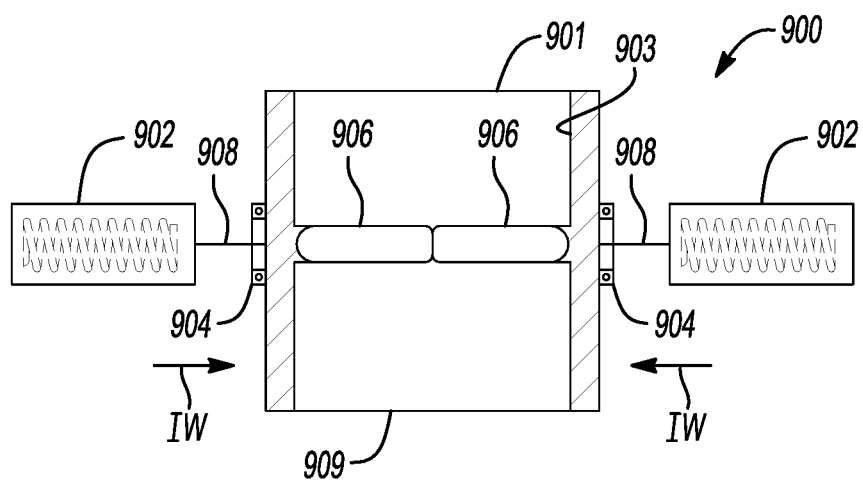
FIG. 3A is a schematic cross-sectional view of an electronically controlled check valve using electromagnetic actuators, where the check valve is in a closed state.
Figure 3B:
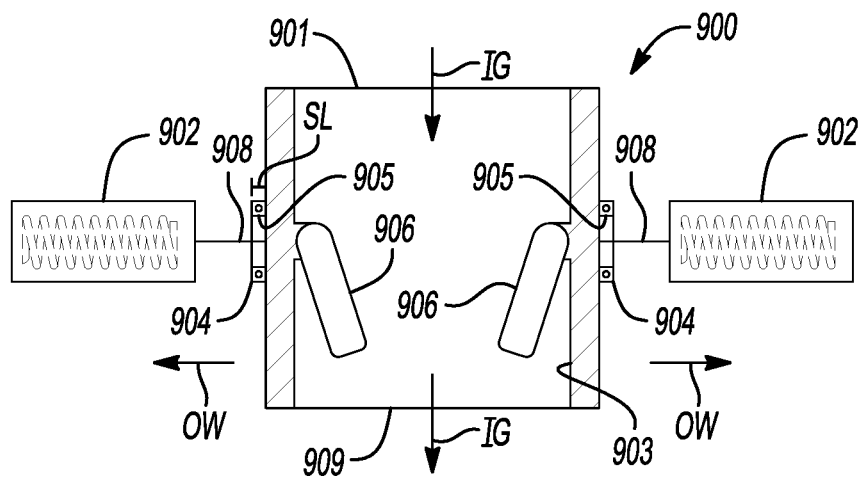
FIG. 3B is a schematic cross-sectional view of the electronically controlled check valve of FIG. 2A in an open state.
Figure 3C:
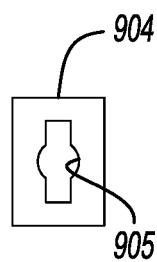
FIG. 3C is a front view of a latch of the electronically controlled check valve of FIG. 2A.
Figure 4D:
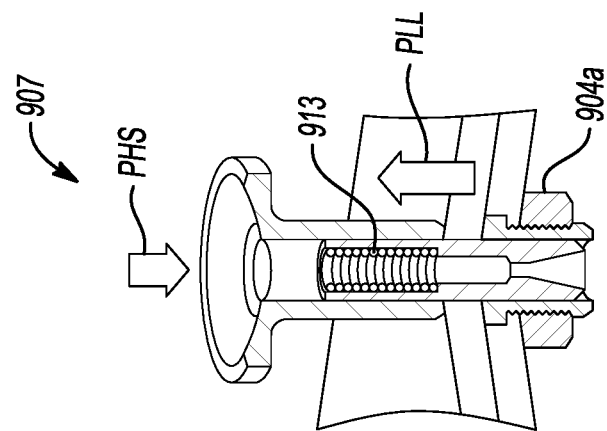
FIG. 4D is a schematic, cross-sectional perspective view of the actuator of FIG. 4A moving from the engaged position toward the disengaged position.
Figure 4C:
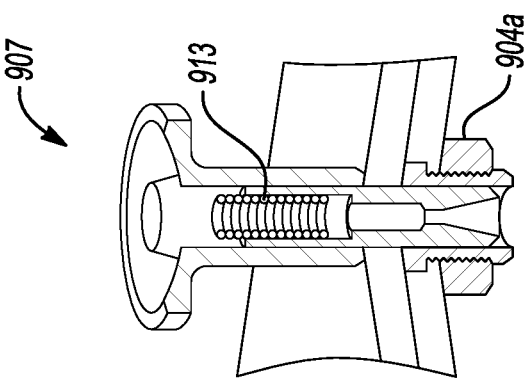
FIG. 4C is a schematic, cross-sectional perspective view of the actuator of FIG. 4A, wherein the actuator is in an engaged position.
Figure 4B:
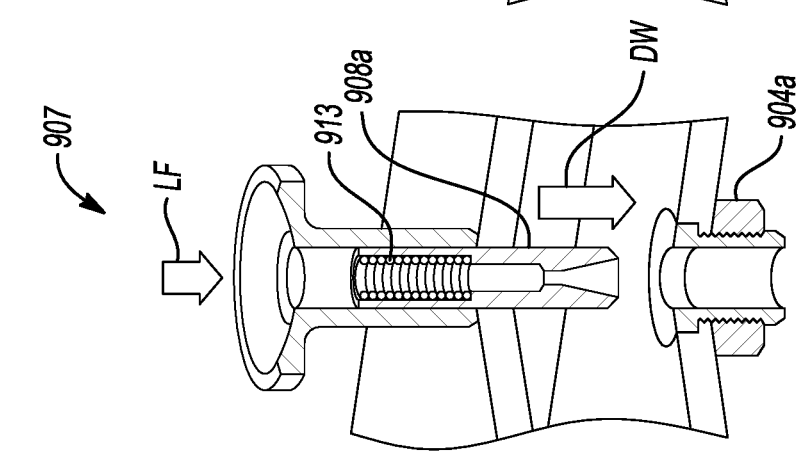
FIG. 4B is a schematic, cross-sectional perspective view of the actuator of FIG. 4A, wherein the actuator is in a disengaged position.
Figure 4A:
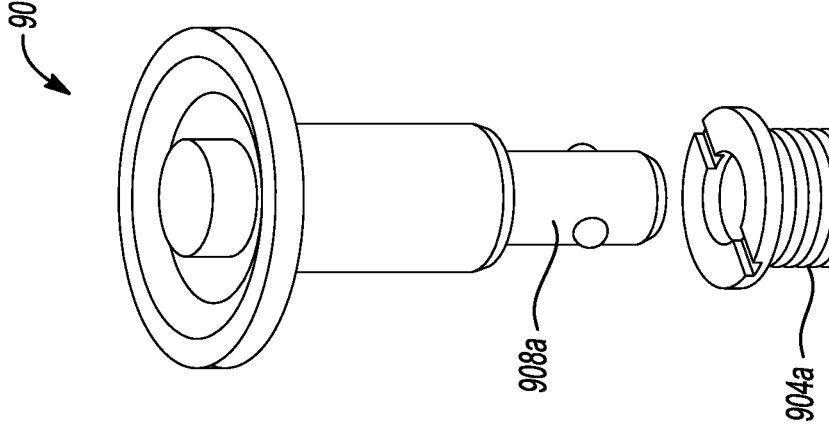
FIG. 4A is a schematic exploded view of an actuator for the electronically controlled valve of FIG. 2A.

With reference to FIGS. 2A and 2B, a check valve actuation system 800 for ventilatory output using ultra-low-pressure gas sources is described. The valve arrangement 501 of the ventilator 700 can include the check valve actuation system 800. A low-pressure input oxygen or compressed air gas flow of 6 LPM, for example, can be used with exemplary gas source pressures of 0.2 PSIG±0.05 PSIG. A check valve 802 with 0.3 PSIG cracking pressure and 0.25 inch diameter can be selected. A pressure actuator 804 is coupled to the check valve 802 and can be used to open the check valve 802 initially by creating a minimum flow (e.g., 0.1 LPM) required to actuate the check valve 802 at the cracking pressure of 0.3 PSIG. The check valve 802 is configured to be then be kept open during the period of useful respiration through a plurality of methods. For example, the check valve 802 is positioned relative to the tubing 503 in a vertical position such that only the pressure actuator 804 can open the check valve 802. The valve 502 can be the check valve 802, and the check valve 802 can be in direct fluid communication with the tubing 503 to allow the input gas IG to enter the check valve 802. The end of the check valve 802 is capped and then the input gas IG can flow through horizontally through a valve inlet 806 and then through an open check valve flap 808. The valve inlet 806 is in direct communication with the tubing 503 to allow fluid from the input gas IG to the check valve 802. The flap 808 includes a first flap portion 812 and a second flap portion 814. The check valve 802 includes a sidewall 810, and the valve inlet 806 extends through the valve inlet 806. Each of the first flap portion 812 and the second flap portion 814 is pivotally connected to the sidewall 810, thereby allowing the flap 808 to move between a closed state (FIG. 8A) to an open state (FIG. 8B). The open check valve flap 808 can be thick (e.g., 0.2 inches) but it has low resistance/low cracking pressures to allow easy opening by the pressure actuator 804. The pressure actuator 804 can be, for example, a pneumatic actuator and is configured to actuate the check valve 802. The check valve 802 is in a vertical orientation relative to the tubing 503 to allow only the pressure supplied by the pressure actuator 804 to open the check valve 802. Upon actuation of the pressure actuator 804, the check valve 802 switches from an OFF or closed state to an ON or open state. Specifically, upon actuation of the pressure actuator 804, a downward actuating pressure AP is exerted on the flap 808, causing the flap 808 to move from the closed state (FIG. 2A) to the open state (FIG. 2B). When the check valve 802 is in the ON or open state, the input gas IG can flow through the flap 808 from the tubing 503 and then curve downward through a tube, which is formed by the sidewall 810, that connects to the outlet 807 of the check valve 802. The check valve 802 allows the flow of input gas IG from the inlet 704 to the flow outlet airline 520, but precludes flow of gas from the flow outlet airline 520 to the inlet 704. The controller 504 can be in electronic communication with the check valve 802 and the pressure actuator 804 to control the operation of the check valve 802. For instance, the controller 504 can command the check valve 802 to open or close.

The pressure actuator 804 can include metal or rubber bellows, air cylinders, pneumatic pistons, servo motors, electromagnetic coils, oscillators, hydraulic actuators, air volume tanks, turbines, air blowers, and other fluid power mechanisms to pressurize a volume of gas at low or high frequency, or actuate the check valve 802. The pressure actuator 804 can include a micro-blower 816 that utilizes a high frequency piezoelectric oscillator that vibrates at 28 kHz frequency such that a mean effective pressure (MEP) is created. This generated MEP can be in the form of an oscillatory pressure waveform. The latency of the mechanical response of the check valve 802 to pressure changes can be slower than the electrical response of the piezoelectric oscillators. This generated MEP can be electronically controlled (through the controller 504) by turning the micro-blower 816 ON or OFF. For example, a MOSFET switch (not shown) can be used to turn the micro-blower 816 ON or OFF to increase pressure in the small chamber/volume (in the check valve 802) by the user or machine. The air accumulates at the valve inlet 806 of the check valve 802 just enough to exceed the cracking pressure of the check valve 802 during the useful phase of respiration, while also minimizing energy consumption of the micro-blower 816.

When the check valve 802 is in the closed state, the edges of the flap 808 prevent the flow of input gas IG through the check valve 802, reducing the amount of volume that needs to be pressurized to actuate the check valve 802 using the pressure actuator 804. The check valve 802 also has an air channel 818 defined on an inner valve surface 820 of the check valve 802. The air channel 818 has a ring-shaped and can therefore extend along the entire circumference of the inner valve surface 820. Further, the air channel 818 has a convex shape. The air channel 818 is disposed around the first flap portion 812 when the check valve 802 is in the closed state. The first flap portion 812 covers the valve inlet 806, thereby preventing the input gas IG from entering the check valve 802 through the valve inlet 806. When the check valve 802 is in the open state, the first flap portion 812 no longer covers the valve inlet 806 and therefore the valve inlet 806 is open. As a consequence, the input gas IG can flow from the tubing 503 to the check valve 802 through the valve inlet 806. Then, due to the convex shape of the air channel 818 the input gas IG, a convex gas flow profile is created along the air channel 818. As such, the input gas IG is outputted through the check valve 802 in an unrestricted flow pattern via the valve inlet 806. The thickness of the first flap portion 812 is equal to or greater than the diameter of the valve inlet 806 (e.g., orifice), allowing the first flap portion 812 to block the valve inlet 806 when the check valve 802 is in the closed state.

The check valve 802 can be in a horizontal-flow-through orientation relative to the tubing 503, such that the pressure actuator 804 can increase the pressure in a small section of the tubing 503 right before the check valve 802 to, for example, 0.3 PSIG. In such case, adding energy to increase the pressure inside the tubing 503 can be beneficial to move the input gas IG to exceed the cracking pressure of the check valve 802. Using ideal gas state equations such as $\Delta E = RT[(P0/P1)-1+\ln(P1/P0)]$, and then translating the flow rate into volume and then mass using known densities for air at certain temperatures, it can be calculated that 10 Wh of power consumption would, causing the check valve actuation system 800 to continuously increase the pressure of the input gas IG by 0.1 PSIG. The power consumption can be reduced if the variance in pressures from the input gas IG is significantly smaller.

The check valve 802 can be electronically controlled to have variable cracking pressures. To do so, a notch, for example, can be embedded in the edge of the flap 808. A heating element can be used. By heating the flap 808, the edge of the flap 808 expands and is locked in by the notch (not shown), closing the check valve 802. The heating would be based on the coefficient of thermal expansion of the material of the flap 808. The check valve 802 allows the input gas IG to flow from the inlet 704 to the flow outlet airline 520, but precludes flow of gas from the flow outlet airline 520 to the inlet 704 to provide the proper amount of output gas OG to the user of the ventilator 700.

Check valve 802 and the check valve actuation system 800 can not just be useful for ventilator or respiratory device applications, but also in applications such as industrial automation. For example, some high pressure compressed air systems can be replaced with lower pressure blower based compressed air systems to reduce energy consumption by >20% using the check valve 802 with compact size profiles, low power requirements, and large orifice sizes. The check valve 802 and the check valve actuation system 800 can be in electronic communication with the controller 504. As such, the controller 504 can command the check valve 802 to open or close.

With reference to FIGS. 3A, 3B, 3C, 4A, 4B, 4C, and 4D, an electronically controlled check valve 900 that utilizes electromagnetic actuator 902 is described. The valve arrangement 501 of the ventilator 700 can include the electronically controlled check valve 900 and the electromagnetic actuator 902. These can include piezoelectric actuators, electromagnetic coils, linear motors, servo motors. Other types of actuators can also be utilized. Some electronically controlled solenoid valves have small orifice sizes due to the fact that generally a shaft or pin needs to be accelerated by an electromagnetic coil, which creates limitations and tradeoffs related to power consumption, response times, and orifice diameter. For example, a 0.5 inch diameter orifice electromagnetic solenoid valve would require a large coil and high power consumption to accelerate the shaft or pin such that response times are <100 milliseconds. Some passive check valves do not consume any power and have large orifices, such as 0.5 inch in small form factors, and cannot be electronically controlled. The electronically controlled check valve 900 seeks to solve these problems. The electronically controlled check valve 900 includes a mechanical latch 904 and an electromagnetic actuator 902, such that a large orifice (between the flaps 906) can be opened, for example >50%, while only having to accelerate a shaft 908 a distance of <25% the length SL of the orifice 905. These numbers are only examples.

The electronically controlled check valve 900 includes one or more of the following: flaps 906, electromagnetic actuator(s) 902, and one or more mechanical latch 904. The electromagnetic actuator 902 operates by linearly accelerating a shaft 908 using electromagnetic forces from a coil through a mechanical latch 904 with an orifice 905 having a particular cutout pattern with tolerances such that the shaft 908 will easily slide through the orifice 905 to selectively contact the flaps 906. To move the electronically controlled check valve 900 toward the closed state, the electromagnetic actuators 902 move the shaft 908 toward an internal cavity 903 of the electronically controlled check valve 900 in the direction indicated by arrows IW. The inward movement (in the direction IW) of the shaft 908 causes the flaps 906 to close, thereby precluding the input gas IG from flowing from a check valve inlet 901 to a check valve outlet 909 of the electronically controlled check valve 900 through the internal cavity 903. This shaft 908 is generally circular in shape and is machined to include two rectangular notches that exceed the outer diameter of the shaft 908. Once the shaft 908 enters the mechanical latch 904 in the proper position, such as after the backplate, the electromagnetic actuator 902 rotates the shaft 908 a quarter turn or 90 degrees to lock the check valve flaps 906 in place in the closed position due to the mechanical properties of mechanical latch 904, similar to turning a key. This turning mechanism can be controlled using a separate or integrated servo motor or rotary actuator (not shown), wherein the rotational position of the actuator can be measured and controlled, using a hall effect sensor or other means of sensing. This mechanical latch 904 can be placed in a variety of positions below or above the inlet of the check valve flaps 906, including but not limited to: near the center, near the edge of the flap, straight down, straight up, slanted at a positive 57 degree angle, slanted at a negative 80 degree angle, slanted at a positive 15 degree angle. This should be mechanically designed in such a way that the travel distance of the shaft 908 is minimized. The electromagnetic actuator 902 can be a rotary actuator and can include components, which can be micro or nanofabricated and/or machined, including but not limited to: electrostatic actuators, thermal actuators, electromagnetic rotors, fluidic actuators. For example, a solenoid armature can be designed such that the armature can be rotated back and forth in a linear or non-linear pattern at high cyclical frequency such that position can be precisely controlled, similar to the actuator and head mechanism found in hard disk drives or HDDs. Consequently, the mechanical latch 904 can be easily and quickly released and/or held in place at a cyclical rate, and/or various durations of time. It is contemplated that the electromagnetic actuator 902 can include a guide screw (not shown). As such, the electromagnetic actuator moves the shaft 908 linearly across a guide screw at a precise position at high linear speed using fast rotational speeds. The rotational position of the shaft 908 can be measured using a hall effect sensor or other means of sensing such as force or position when lightly contacting the face of mechanical latch 904. The direction of rotation of the electromagnetic actuator 902 can be reversed such that the shaft 908 can be moved back and forth using the guide screw. The shaft 908 can be released from mechanical latch 904 and rotate counterclockwise down the guide screw using the recoil force from a spring (not shown) that is actuated by rotating the shaft 908 using the guide screw. Actuating the electromagnetic actuators 902 causes the shaft 908 to move outwardly (in the direction of arrows OW), causing the flaps 906 to pivot to the open position. In the open position, the flaps 906 allow the input gas IG to flow from the check valve inlet 901 to the check valve outlet 909 through the internal cavity 903 of the electronically controlled check valve 900.

With reference to FIGS. 4A, 4B, 4C, and 4D, the pin 908a and the latch 904a can be configured as a "button locking" pin latch mechanism 907. In such case, only a linear solenoid or actuator, and no rotary or combo rotary and linear motion actuator, is required. Electromagnetic actuator 902 (FIG. 3A) exerts a linear force LF to accelerate a pin 908a into a latch 904a. As a result, the pin 908a moves in a downward direction DW into the latch 904a and is clamped into place by the latch 904a. The pin 908a can be contained inside or have a spring 913 around the pin 908a. As such, when the electromagnetic actuator 902 (e.g., linear solenoid actuator) pushes (as is shown by arrow PHS) on the pin 908a after clamped into place by the latch 904a, the pin 908a would be pulled (in the direction PLL) by the recoil force of the spring. Only one electromagnetic actuator 902 can be required such that a mechanical latch 904 can hold both flaps 906 closed when the shaft 908 is clamped into the latch 904. In one embodiment, one or more mechanical latch 904 are proximal to the flaps 906, such that a portion or the entirety of the pin latch mechanism 907 is embedded or comprise the flaps 906, such that the distance of linear travel between mechanical latch 904 and the flaps 906 is minimized, for example less than 1 mm travel distance.

The electronically controlled check valve 900 can not just be useful for ventilator or respiratory device applications, but also in applications such as industrial automation. For example, some high pressure compressed air systems can be replaced with lower pressure blower based compressed air systems to reduce energy consumption by >20% using electronically controlled check valve 900 with compact size profiles, low power requirements, and large orifice sizes. The electronically controlled check valve 900 and the electromagnetic actuator 902 can be in electronic communication with the controller 504. As such, the controller 504 can command the electronically controlled check valve 900 to open or close.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Accordingly, the disclosure and the figures are to be regarded as illustrative rather than restrictive.

What is claimed is:

1. A check valve, comprising:
   a valve inlet;
   a valve outlet;
   a flap disposed between the valve inlet and the valve outlet;
   an electromagnetic actuator coupled to the flap, wherein the actuator comprises a micro-blower configured to generate a mean effective pressure using a high-frequency piezoelectric oscillator;
   a controller configured to control an open-closed state of the check valve; and
   a flow sensor configured to measure a gas output, wherein the flow sensor is in electric communication with the controller;
   wherein the check valve is configured to allow an input gas to flow from the valve inlet to the valve outlet when the check valve is in the open state;
   wherein the check valve is configured to preclude the input gas from flowing from the valve inlet to the valve outlet when the check valve is in the closed state;
   wherein, upon actuation of the electromagnetic actuator, the flap moves away from the valve inlet to allow the input gas to flow from the valve inlet to the valve outlet of the check valve; and
   wherein the mean effective pressure comprises an oscillatory pressure waveform, and wherein the generated mean effective pressure is electronically controlled by power cycling the microblower.

2. The check valve of claim 1, wherein the electromagnetic actuator further includes a shaft coupled to the flap such that actuation of the electromagnetic actuator causes the shaft to move away or toward the valve inlet.

3. The check valve of claim 2, further comprising a latch configured to retain the shaft, wherein the latch is configured to retain the shaft in position.

4. The check valve of claim 3, wherein the shaft is movable relative to the latch such that movement of the shaft relative to the latch causes the check valve to move between the open state and the closed state.

5. The check valve of claim 4, wherein the latch has an orifice having a length, and moving the shaft less than twenty-five percent of the length of the orifice of the latch causes the check valve to open at least fifty percent of a maximum capacity of the check valve.

6. A ventilator, comprising:
   a tubing configured to receive an input gas;
   a flow outlet airline in fluid communication with the tubing, wherein the flow outlet airline includes an airline outlet, and the flow outlet airline is configured to supply an output gas to a user via the airline outlet;
   a breath detection airline including an airline inlet, wherein the airline inlet is separated from the airline outlet of the flow outlet airline, and the breath detection airline is configured to receive breathing gas from the user during exhalation by the user via the airline inlet;
   a pressure sensor in direct fluid communication with the breath detection airline, wherein the pressure sensor is configured to measure breathing pressure from the user, and the pressure sensor is configured to generate sensor data indicative of breathing by the user; and
   a valve arrangement coupled to the tubing, wherein the valve arrangement includes a check valve in fluid communication with the tubing to control a flow of the inlet gas through the tubing, the check valve comprising:
   a valve inlet;
   a valve outlet;
   a flap disposed between the valve inlet and the valve outlet;
   a controller configured to control an open-closed state of the check valve;
   an electromagnetic actuator coupled to the flap, wherein the actuator comprises a micro-blower configured to generate a mean effective pressure using a high-frequency piezoelectric oscillator;
   wherein the check valve is configured to allow an input gas to flow from the valve inlet to the valve outlet when the check valve is in the open state;
   wherein the check valve is configured to preclude the input gas from flowing from the valve inlet to the valve outlet when the check valve is in the closed state;
   wherein, upon actuation of the electromagnetic actuator, the flap moves away from the valve inlet to allow the input gas to flow from the valve inlet to the valve outlet of the check valve; and
   wherein the mean effective pressure comprises an oscillatory pressure waveform, and wherein the generated mean effective pressure is electronically controlled by power cycling the microblower.

7. The ventilator of claim 6, wherein the electromagnetic actuator further includes a shaft coupled to the flap such that actuation of the electromagnetic actuator causes the shaft to move away or toward the valve inlet.

8. The ventilator of claim 7, further comprising a latch configured to retain the shaft, wherein the latch is configured to retain the shaft in position.

* * * * *